(12) United States Patent
Koltermann et al.

(10) Patent No.: US 9,005,936 B2
(45) Date of Patent: Apr. 14, 2015

(54) LIQUEFIED BIOMASS

(75) Inventors: Andre Koltermann, Icking (DE); Markus Rarbach, Munich (DE); Thomas Bruck, Ebenhausen (DE); Jochen Gerlach, Munich (DE); Isabel Unterstrasser, Rimsting (DE); Andreas Kohl, Munich (DE); Zdravko Dragovic, Munich (DE); Ulrich Kettling, Munich (DE)

(73) Assignee: Süd-Chemie IP GmbH & Co. KG, Munich (DE)

( * ) Notice: Subject to any disclaimer, the term of this patent is extended or adjusted under 35 U.S.C. 154(b) by 0 days.

(21) Appl. No.: 13/322,395

(22) PCT Filed: May 21, 2010

(86) PCT No.: PCT/EP2010/057045
§ 371 (c)(1),
(2), (4) Date: Jan. 24, 2012

(87) PCT Pub. No.: WO2010/136404
PCT Pub. Date: Dec. 2, 2010

(65) Prior Publication Data
US 2012/0135475 A1    May 31, 2012

(30) Foreign Application Priority Data
May 25, 2009    (EP) .................................... 09161030

(51) Int. Cl.
*C12P 19/14* (2006.01)
*C12P 19/02* (2006.01)
*C12P 1/04* (2006.01)
*C12P 1/02* (2006.01)
*C07H 3/02* (2006.01)

(52) U.S. Cl.
CPC ................. *C12P 19/02* (2013.01); *C12P 19/14* (2013.01); *Y02E 50/17* (2013.01)

(58) Field of Classification Search
USPC .......................................................... 435/99
See application file for complete search history.

(56) References Cited

U.S. PATENT DOCUMENTS

| | | | |
|---|---|---|---|
| 4,338,399 A | 7/1982 | Weil et al. | |
| 4,886,672 A * | 12/1989 | de Baynast de Septfontaines et al. | 426/48 |
| 7,244,409 B2 | 7/2007 | Burgfels et al. | |

FOREIGN PATENT DOCUMENTS

| | | |
|---|---|---|
| WO | WO-9529598 A1 | 11/1995 |
| WO | WO 2008/113585 | 9/2008 |

OTHER PUBLICATIONS

Olsson, L. and Hahn-Hagerdal, H. "Fermentation of lignocellulosic hydrolysates for ethanol production" (1996) Enzyme and Microbial Technology 18:312-331.*
D'Souza, S. et al. "Continuous Conversion of Sucrose to Fructose and Gluconic Acid by Immobilized Yeast Cell Multienzyme Complex" (1980) Biotechnology and Bioenginerring 22:2179-2189.*
Wen et al. "Isolation and characterization of hemicellulose and cellulose from sugar beet pulp" 1988 Journal of Food Science 53 826-829.*
Berlin et al., "Optimization of enzyme complexes for lignocellulose hydrolysis", Biotechnology and Bioengineering, vol. 97, pp. 287-296, 2007.
Bethune Doran et al., "Fermentations of pectin-rich biomass with recombinant bacteria to produce fuel ethanol", Applied Biochemistry and Biotechnology, vol. 84-86, pp. 141-152, 2000.
Bonnin et al., "Enzymic release of cellobiose from sugar beet pulp, and its use to favour vanillin production in *Pycnoporus cinnabarinus* from vanillic acid", Carbohydrate Polymers, vol. 41, pp. 143-151, 2000.
Bradford M.M., "A rapid and sensitive method for the quantitation of microgram quantieis of protein utilizing the principle of protein-dye binding", Anal. Biochem., vol. 72, pp. 248-254, 1976.
Chen, W.P. et al., "Purification and some properties of beta-1, 3-xylanase from *Aspergillus terreus* A-07", Agric. Biol. Chem., vol. 50, pp. 1183-1194, 1986.
Ezeji T.C. et al., "Butanol fermentation research: upstream and downstream manipulations", The Chemical Record, vol. 4 No. 5, pp. 305-314, 2004.
Fernandes et al.: "Enzyme systems from the thermophilic fungus *Talaromyces emersonii* for sugar beet bioconversion", Bioresources, vol. 3, pp. 898-909, 2008.
Hernandez-Salas et al., "Comparative hydrolysis and fermentation of sugarcane and agave bagasse," Bioresource Technology, vol. 100, pp. 1238-1245, 2009.
Jing X. et al., "Inhibitor performance of lignocellulose degradation products on industrial cellulose enzymes during cellulose hydrolysis", Appl. Biochem. Biotechnol., vol. 159, pp. 696-707, 2009.
Kumar et al., Bioconversion of lignocellulosic biomass: biochemical and molecular perspectives, Journal of Industrial Microbiology and Biotechnology, vol. 35, pp. 377-391, 2008.
Markov et al., "New effective method for analysis of the component composition of enzyme complexes from Trichoderma reesei", Biochemistry (Moscow), vol. 70, p. 1, 2005.
Oosterveld A. et al., "Enzymatic modification of pectic polysaccharides obtained from sugar beet pulp", Carbohydrate Polymers, vol. 48, pp. 73-81, 2002.
Petersen et al.: "Development of a polysaccharide degrading strain of *Saccharomyces icerevisiae*", Biotechnology Techiques, vol. 12, pp. 615-619, 1998.

(Continued)

*Primary Examiner* — Suzanne M Noakes
*Assistant Examiner* — Gerard Lacourciere
(74) *Attorney, Agent, or Firm* — McCarter & English, LLP; Danielle L. Herritt

(57) ABSTRACT

The invention is directed to a liquefied sugar beet and/or sugar cane biomass material as well as production methods and uses thereof. The liquefied biomass is storage stable and can be used for the production of a product resulting from fermentation.

14 Claims, 7 Drawing Sheets

(56) References Cited

OTHER PUBLICATIONS

Rattanachomsri et al.: "Simultaneous non-thermal saccharification of cassava pulp by multi-enzyme activity and ethanol fermentation by *Candida tropicalis*", Journal of Bioscience and Bioengineering, vol. 107, pp. 448-493, 2009.

Sakamoto T. et al., "Analysis and structure of sugar-beet pectins by enzymatic methods", Phytochemistry, vol. 39, pp. 821-823, 1995.

Sillers R. et al., "Metabolic engineering of the non-sporulating, non-solvatogenic *Clostridium acetobutyricum* strain M5 to produce butanol without acetone demonstrate the robustness of the acid-formation pathways and the importance of the electron balance", Metabolic Engineering, vol. 10, pp. 321-332, 2008.

Spagnuolo et al: "Synergistic effects of cellulolytic and pectinolytic enzymes in degrading sugar beet pulp", Bioresource Technology, vol. 60, pp. 215-222, 1997.

Taguchi H. et al., "A simple assay for xylanase using o-nitrophenyl-beta-D-xylobioside", Bioscience, Biotechnology, and Biochemistry, vol. 60, pp. 983-985, 1996.

Woskow et al., "Propionic acid production by a propionic acid-tolerant strain of *Propionibacterium acidipropionici* in Batch and semicontinuous fermentation", Appl. Envir. Micorbiol., vol. 57, pp. 2821-2828, 1991.

Wood T.M. et al., "Methods fo measuring cellulase activities", Methods in Enzymology, vol. 160, pp. 87-112, 1988.

European Search Report for EP 09 16 1030 dated Nov. 2, 2009.

International Search Report for PCT/EP2010/057045 dated Dec. 22, 2010.

Maloney, et al.: "Enzymic Saccharification of Sugar Beet Pulp"; Biotechnology and Bioengineering; 1984; vol. 26, pp. 714-718.

Grachev I.M., "Technology of enymic preparations",; revised and enlarged second edition, Moscow, "Elevar", p. 331, 2000.

\* cited by examiner

LIQUEFIED BIOMASS

RELATED APPLICATIONS

This application is a 35 U.S.C. §371 national stage filing of International Application No. PCT/EP2010/057045, filed May 21, 2010, which is related and claims priority to EP Application Serial No.: 09161030.3, filed May 25, 2009. The entire contents of these applications are explicitly incorporated herein by reference.

FIELD OF INVENTION

The invention is directed to a liquefied sugar beet and/or sugar cane biomass material as well as production methods and uses thereof.

TECHNICAL BACKGROUND AND PRIOR ART

Sugar beet (*Beta vulgaris*) and sugar cane (*Saccharum* sp.) are valuable sources for refined sugar such as liquid or crystalline sucrose for industrial and consumer use. Sugar beet roots contain sucrose and sugar beet pulp, the latter containing pectin, cellulose and hemicellulose. Sugar cane contains sucrose and sugar cane pulp, the latter containing cellulose, hemicellulose, pectins and lignin. The sugar refining process is a process for extracting sucrose from either sugar beet or sugar cane followed by the removal of impurities and crystallization of sucrose. After the removal of mud, sand, weeds, and leaves, sugar beets are fed into slicers and cut into long pieces called cossettes. The cossettes are discharged into a scalding tank leading to the diffuser. Here the sugar is removed from the cossettes by being dissolved in hot water in a continuous counter-flow process. Products of this process are the sugar solution called raw juice and the so-called beet pulp, the latter being dried in a pulp dryer. The raw juice moves through various stages of purification and filtration to remove impurities and non-sugar substances to yield thick juice (65-70% d.s. content) or, after crystallization, refined fine sugar. Besides being refined to crystalline sugar, sucrose in the form of raw sugar or thick juice is a valuable fermentation substrate for the biotechnological production of chemicals and biomolecules. Due to the costly refinery process, the use of sucrose and other sugars as fermentation feedstocks for the production of products such as fuels or polymer building blocks is relatively expensive. Cheaper fermentation substrates are therefore desirable.

Sugar beet biomass can not efficiently be used for typical fermentation processes such as ethanol, butanol, lactic acid or propionic acid production without additional treatment to liquefy the biomass and hydrolyze polymers.

Chemical treatment processes for the liberation of monomeric sugars and sucrose from cellulose-, pectin- and hemicellulose-containing biomass such as sugar beet biomass have been described. Unselective processes such as sulphuric acid treatment can be used to hydrolyze sugar beet biomass; however such treatment is inefficient at low temperatures. At higher temperatures (e.g. dilute acid steam pretreatment at 200-250° C.) it leads to inhibitory components such as hydroxymethylfurfural (HMF) or furfural that render a subsequent fermentation process problematic (Jing et al., 2009).

U.S. Pat. No. 4,886,672 (Baynast et at) describes a process for liquefaction of sugar beet biomass by enzymatic treatment. The process includes washing and coarse grinding of sugar beet biomass, mixing the ground product with an enzymatic mixture, adjusting the pH to 3 to 5.5, additional fine grinding the substrate and recovering the resulting liquid. The enzyme mixture used in this process contains at least one "SPS-ase" ("SP 249", an enzyme preparation obtained from *Aspergillus aculeatus*), one cellulase ("Celluclast", an enzyme preparation obtained from *Trichoderma reesei*) and one cellobiase ("Novo 188", an enzyme preparation obtained from *Aspergillus niger*). In this process, bacteriostatic agents such as formal may be added. While the addition of such bacteriostatic agents is undesirable for subsequent fermentation processes using the liquefied biomass, their addition is described to be essential to avoid microbial proliferations, e.g. to provide a storage stable biomass.

SUMMARY OF THE INVENTION

It is thus the object underlying the present invention to provide a process for producing of a biomass that can be used in a subsequent fermentation process even after prolonged storage.

In a first aspect, the invention thus provides a process for the production of a liquefied biomass, comprising the following steps:
(a) Providing solid biomass derived from sugar beet and/or sugar cane;
(b) Liquefying said biomass by subjecting it to an enzyme mixture comprising cellobiohydrolase, beta-glucosidase, and polygalacturonase activity to a liquefied biomass with a content of remaining insoluble solids of less than 2% (w/w).

In a preferred embodiment of the invention, a chemical or microorganism is added to render the liquefied biomass storage stable.

In a particularly preferred embodiment of the invention, the chemical or microorganism is added before or during step (b).

The chemical is preferably an acid which is added in an amount to adjust the pH of the liquefied biomass to a pH below 3.

The invention also provides a liquefied biomass derived from sugar beet and/or sugar cane, which is storage stable and fermentable, particularly one that is obtainable by the process of the present invention. This liquefied biomass can be used for the production of a product resulting from fermentation.

In another aspect, the invention thus provides a process for the production of a liquefied biomass, comprising the following steps:
(a) Providing solid biomass derived from sugar beet and/or sugar cane;
(b) Liquefying said biomass by subjecting it to an enzyme mixture comprising cellobiohydrolase, beta-glucosidase, and polygalacturonase activity to a liquefied biomass with a content of remaining insoluble solids of less than 2% (w/w); and
(c) Fermentation of the sugars released from the liquefied biomass to one or more fermentation products.

In a preferred embodiment of this aspect, steps (b) and (c) are performed simultaneously.

In another preferred embodiment of the invention, a chemical or microorganism is added to render the process material storage stable.

FIGURES

DETAILED DESCRIPTION OF THE INVENTION

Figure 1:
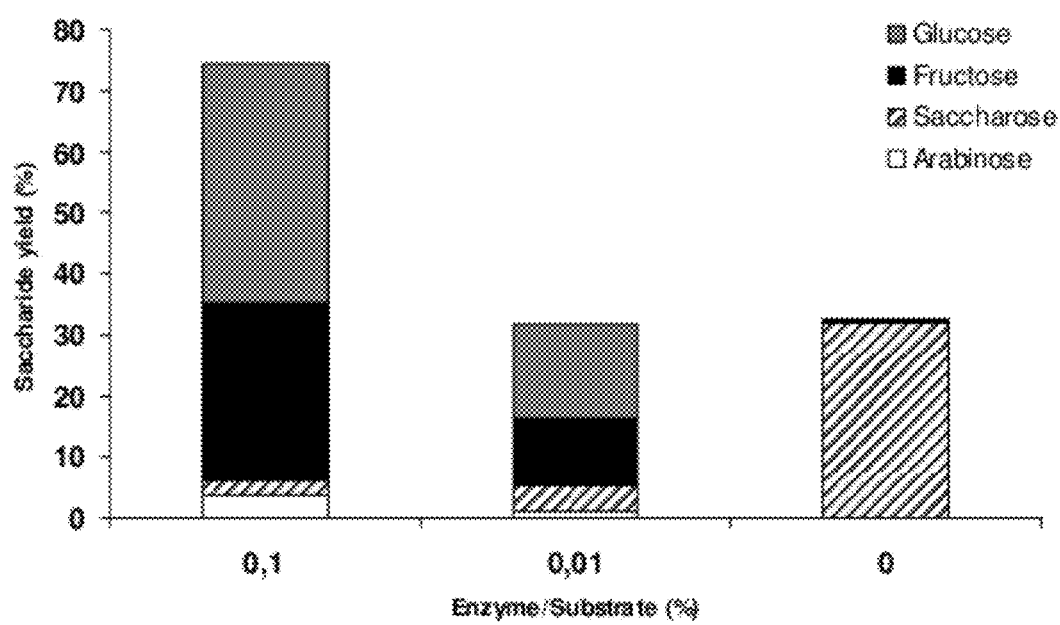
FIG. 1 shows the influence of enzyme dosing on sugar composition and yield

In step (a) of the process of the present invention, sugar beet biomass and/or sugar cane biomass is provided.

The term "sugar beet biomass" refers to the complete and unprocessed root tissue of *Beta vulgaris* including the outer peel and the internal pulp. Dry tissue of *Beta vulgaris* contains 80% (w/w) soluble sucrose, while beet pulp is made up of approximately 90% polymeric sugars, including 7% pectin, 7% cellulose, and 7% hemicellulose in the form of arabinan. The term "sugar cane biomass" refers to the complete and unprocessed stalks of *Saccharum* sp. including the outer peel and the internal pulp. Dry tissue of *Saccharum* sp. contains 80% (w/w) soluble sucrose, while dry cane bagasse is made up of approximately 70% polymeric sugars, including 45% cellulose, 23% lignin and 25% hemicellulose primarily in the form of xylan.

The biomass is preferably washed prior to subjecting it to the enzymatic treatment, and washing water is removed prior to further processing. Moreover, it is preferred to provide the biomass in particulate form e.g. by cutting the biomass prior to step (b), preferably in the form of cossettes. The size of the biomass particles is preferably such that 90% (w/w) or more of the particles have a maximum length of at least 1 mm, more preferably 10 to 200 mm. In case of disc-shaped particles, the diameter is preferably at least 1 mm. However, the biomass is preferably not ground prior to or during step (b).

For the liquefying step, the biomass is added with a dry solid content of preferably 5 to 30% (w/w), more preferably 15 to 25% (w/w). The term "dry solid" (d.s.) refers to the mass to biomass ratio determined after water removal from fresh tissue using an IR-balance.

Prior to subjecting the solid biomass to step (b), it may be frozen, although this is generally neither necessary nor desirable.

In process step (b), the solid biomass, preferably in particulate form, is then liquefied until the content of remaining unsoluble solids is less than 2% (w/w) (preferably less than 1% (w/w), even more preferably less than 0.5% (w/w)) using an enzyme composition or mixture comprising cellobiohydrolase, beta-glucosiclase and polygalacturonase activity. This is the actual liquefaction step. The term "liquefaction" means the hydrolytic conversion of insoluble polymeric substrates to soluble monomeric or oligomeric products by chemical, physical, and/or enzymatic processes such as hydrolysis. The term "polymeric substrate" means substances composed of either a specific monomeric constituent or a limited variety of defined monomeric constituents covalently linked together in a linear or partially branched molecular structure.

The term "activity" of an enzyme refers to the enzyme's catalytic activity under appropriate conditions under which the enzyme serves as a protein catalyst, which converts specific polymeric or artificial substrates to specific oligomeric or monomeric products.

The term "cellobiohydrolase" refers to an enzyme of the E.C. class 3.2.1.91, which catalyses the hydrolysis of polymeric cellulose to cellobiose and other beta-D-glucose oligomers. The cellobiohydrolase activity is preferably provided by a cellulase product that may show, besides cellobiohydrolase activity (CBH I and/or CBH II), one or more of endoglucanase activity (EG I and/or EG II), exo-beta-glucosidase activity and endo-xylanase activity.

The term "polygalacturonase" refers to an enzyme of the E.C. class 3.2.1.15, which catalyses the breakdown of polymeric pectin and polygalacturonic acid to galacturonic acid oligomers and monomeric galacturonic acid. The polygalacturonase activity is preferably provided by a pectinase product that may show, besides the polygalacturonase activity, one or more activities including pectin lyase activity, arabinofucosidase activity, endo-arabinase activity, endo-xylanase activity, pectate lyase activity, pectinmethylesterase activity, polygalacturonidase activity. In a preferred embodiment, the polygalacturonase activity shows an optimum within a pH range of 2 to 7 and an activity of at least 50% of its optimum activity at a pH below 3. In another preferred embodiment, the polygalacturonase activity shows an optimum within a pH range of 2 to 3.

The term "beta-glucosidase" refers to an enzyme of the E.C. class 3.2.1.21, which catalyses the hydrolysis of cellobiose, cellotiose, cellotetraose and other beta-D-glucose oligomers to the corresponding glucose monomer.

The term "pectinmethylesterase" refers to an enzyme of the E.C. 3.1.1.11 class, which catalyses the hydrolysis of methyl substituents from modified polygalacturonan backbone. The term "rhamnogalacturonase" refers to an enzyme of the E.C. 3.2.1 class, which catalyses the hydrolysis of rhamnose substituents of polygalacturonan backbone. The term "1,3-/1,6-D-glucanase" refers to an enzyme of the E.C. 3.2.1 class, which catalyses the hydrolysis hexose substituents of 1,3-/1,6-modified sugar polymers.

The term "enzyme mixture" means a mixture of proteinaceous entities that are able to catalytically convert polymeric or oligomeric substrates into smaller oligomeric or monomeric constituents (building blocks). According to the present invention, the enzyme mixture used in step (b) comprises cellobiohydrolase, beta-glucosidase and polygalacturonase activity.

The enzyme mixture preferably contains 1 to 50% (w/w), preferably 1 to 10%, more preferably 1 to 4% (w/w) cellobiohydrolase, with respect to the total weight of the enzyme mixture. The enzyme mixture preferably contains 1 to 10% (w/w), more preferably 1 to 4% (w/w) beta-glucosidase, with respect to the total weight of the enzyme mixture. The enzyme mixture preferably contains 25 to 75% (w/w), more preferably 35 to 45% (w/w) polygalacturonase, with respect to the total weight of the enzyme mixture. Particularly preferred are enzyme mixtures containing 1 to 50% (w/w) cellobiohydrolase, 1 to 10% (w/w) beta-glucosidase, and 1 to 75% (w/w) polygalacturonase, particularly 30 to 40% (w/w) cellobiohydrolase, 1 to 4% (w/w) beta-glucosidase, and 35 to 45% (w/w) polygalacturonase, with respect to the total weight of the enzyme mixture.

The weight ratio of cellobiohydrolase:beta-glucosidase:polygalacturonase is preferably in the range of 1:(0.01 to 0.2):(0.5 to 10), more preferably in the range of 1:(0.03 to 0.2):(1 to 2).

The enzyme mixture preferably also shows one or more additional hemicellulase or pectinase activities preferably selected from arabinase, xylanase, pectinmethylesterase, rhamnogalacturonase, and 1,3-/1,6-beta-D-glucanase or a combination of arabinase and polygalacturonase with rhamnogalacturonidase and/or pectin lyase. The term "hemicellulase" refers to a collection of hydrolase activities that are responsible for the removal and depolymerization of hemicellulosic residues in biomass (e.g. arabinan, arabinoxylan, galactan and xylan). These enzyme activities comprise arabinase, arabinofucosidase, galactose, galactosidase, xylanase, xylosidase, arabinogalactase and 1,3-/1,6-beta-D-glucanase.

The term "pectinase" refers to a collection of hydrolase, esterase and lyase activities that are responsible for the removal and depolymerization of pectinic residues in biomass (e.g. polygalacturonan, rhamnogalacturonan, xylogalacturonan). These enzyme activities comprise rhamnogalacturonase, polygalacturonase, glucuronidase, pectin lyase, pectinmethylesterase, acetylesterase, acetylgalacturonesterase and pectate lyase.

The term "xylanase" refers to an enzyme of the E.C. class 3.2.1.8, which catalyses the random hydrolysis of polymeric xylan, polymeric pectin, or hemicellulose containing xylose residues resulting in the formation of xylose-containing sugar oligomers and/or monomeric xylose residues. The term "arabinase" refers to an enzyme of the E.C. class 3.2.1.99, which catalyses the random hydrolysis of arabinan and pectinic substances containing arabinose residues to lower oligosaccharides containing arabinose units and monomeric arabinose residues. The term "xylosidase" refers to an enzyme of the E.C. class 3.2.1.37, which catalyses the hydrolysis of xylobiose, xylotriose, xylotetraose, or xylose-containing oligomers to monomeric xylose residues or lower xylose-containing oligomers. The term "arabinofucosidase" refers to an enzyme of the E.C. class 3.2.1.55, which catalyses the hydrolysis of arabinose, arabinotriose, arabinotetraose or other arabinose-containing sugar oligomers to shorter oligomers or monomeric arabinose.

The enzyme mixture preferably lacks any invertase enzyme.

The term "E/S" refers to the mass ratio of total enzyme applied to a certain biomass thy solid (d.s.) content.

The enzyme mixture is preferably added to the biomass in an amount of 0.025 to 4% (w/w) of the biomass, more preferably 0.05 to 0.5% (w/w) of the biomass, particularly preferred being 0.05 to 0.1% (w/w) of the biomass.

In a preferred embodiment, step (b) is carried out for 2 to 100 hours, more preferably 2 to 80 hours, particularly preferred being 2 to 20 hours, even more preferably below 10 hours. The reaction temperature is preferably in the range of 35 to 60° C., more preferably 40 to 50° C. In another preferred embodiment, step (b) is carried out for more than 100 hours, and the reaction temperature is in the range of 10 to 30° C., more preferably the reaction is performed at ambient temperature without heating or cooling.

According to the present invention, a chemical or microorganism is added before or during step (b) to render the liquefied biomass storage-stable. The addition of the chemical or microorganism preferably adjusts the pH of the final liquefied product to a value of less than 3. In a particularly preferred embodiment, the chemical and/or microorganism is added to the solid biomass before or together with the enzyme mixture.

The chemical is preferably an acid, more preferably an inorganic acid such as sulfuric acid. The acid is preferably added in an amount to adjust the pH of the liquefied biomass to a pH below 3, more preferably below 1.5. Chemical agents for the preservation of biomass include but are not limited to mineral acids such as $H_2SO_4$, $H_2SO_3$, HCl, $H_3PO_4$, $H_2CO_3$, $HNO_3$, $HNO_2$ and/or acid anhydrides such as $SO_2$, $CO_2$, which are added 0-4 hours after initiation of enzymatic liquefaction, preferably at concentrations of 0.01-0.1% (v/w), more preferably 0.01-0.03% (v/w). The concentration and time point for addition of these chemical agents is optimized, so that these agents do not decrease the efficiency of the enzymatic liquefaction process and do not lead to sugar degradation products. In a particularly preferred embodiment, the acid is added to the biomass before or together with the enzyme mixture.

In another embodiment of the invention, a microorganism is added before or during step (b) to render the liquefied biomass storage-stable. Preferred microorganisms include one or more selected from lactic acid bacteria, including *Bacilli*, *Lactobacilli* and *Lactococci*, yeast including *Saccharomyces* and alcohol producing bacteria including *Clostridia*, which are capable of producing a preservative. Biological agents that can be added for the preservation of liquefied biomass include but are not limited to *Saccharomyces* sp., *Schizosaccharomyces* sp., *Lactobacillus* sp., *Leuconostoc* sp., *Bifidobacterium* sp., *Clostridium* sp., *Zymomonas* sp., *Escherichia* sp. or *Propionibacterium* sp. Inoculation of sugar beet or sugar cane biomass slurry with these biological agents after initiation of the enzymatic liquefaction process results in the formation of fermentation products, which comprise but are not limited to either ethanol, butanol, acetone, 1,3-propanediol, propanol, acetic acid, lactic acid and propionic acid, which act as preservatives protecting the resulting liquid from spoilage by microorganism. The microbial inoculum size (and exact time point of inoculum addition to the enzymatic liquefaction process) are optimized for each biological agent such that the efficiency of the enzymatic liquefaction process is not reduced. In a preferred embodiment, the microbial inoculum is added to an optical density of $OD_{600nm}=0.1$. Preferably, the microbial inoculum is added at 0-4 hours after starting the enzymatic liquefaction. In a particularly preferred embodiment, the microorganism is added to the biomass before or together with the enzyme mixture. Additionally the resulting fermentation products are formed in minimal amounts under aerobic or anaerobic conditions and without pH control, such that a maximum of sugar released from the biomass is preserved and concurrently the concentration of said fermentation products is sufficient to inhibit growth of all microbial entities. For the described biological preservation process, the pH value is generally self regulating with a final pH below 3, preferably between 1.5 and 2.5 at which the fermentation is self terminating without manual interference. Production of preserving fermentation products under anaerobic conditions poses the additional advantage that no oxygen supply has to be engineered into the storage facility. Therefore the intended storage facility can be a simple agricultural style SILO for biomass storage.

The problems of the prior art for using liquefied sugar beet and sugar cane biomass as cost efficient fermentation media are thus overcome by providing combinations of sequential and/or parallel processes for enzymatic liquefaction and chemical/biological preservation, which allows the use of the liquefied biomass in downstream fermentative processes to produce enzymes and value-added chemicals.

An additional advantage of the presented methodologies is that enzymatic biomass liquefaction and preservation can be carried out in parallel and in a single tank, which provides for a single and cost effective process set-up. Thus, biomass harvest, storage, liquefaction and preservation of the resulting liquid can be consolidated into a single process step. To complete the process of sugar beet/sugar cane biomass liquefaction and preservation it is therefore possible to simply transfer the raw biomass from the field to the storage facility, add liquefaction enzymes, mix these with chemical or biological agents to initiate preservation and finally close the facility to establish an anaerobic environment.

Yet another advantage of the process is that the mild preservation methodologies described herein preserve 90-100% (w/w) of the initial sugar content released by enzymatic liquefaction of sugar beet and sugar cane biomass, which is therefore available for downstream fermentation processes. Yet another advantage of the current process is that in contrast to prior art the liquefied biomass does not contain bacteriostatic agents such as formol or sugar degradation products, such as hydroxymethylfurfural (HMF), which act as fermentation inhibitors in downstream processes.

The invention thus also provides a liquefied sugar beet and/or sugar cane biomass material, which is storage stable and fermentable. This biomass material is preferably obtainable by the process of the present invention. Its preferred pH is below 3, preferably in the range of 1.5 to 2.5. Its sugar content is preferably below 65% (w/w), with respect to the total mass of the liquefied product. Its sucrose content is preferably in the range of 0 to 90% (w/w), more preferably 0 to 50% (w/w), its fructose content is preferably in the range of 0 to 45% (w/w), more preferably 20 to 45% (w/w), and its glucose content is generally in the range of 0 to 70% (w/w), preferably 50 to 70% (w/w), each with respect to the total sugar content. In a preferred embodiment, the sucrose content is below 10% (w/w) and the glucose and fructose content is above 45% (w/w) and 40% (w/w), respectively, of total sugar content. The sum of fructose content and glucose content is preferably above 90° A) (w/w) of total sugar content. The storage stability can be achieved without sterilization by heat treatment or concentration of the resulting liquid from process step (b).

A liquefied biomass material is deemed to be storage stable if the increase in colony forming units that are detected on solid LB agar plates after storage of 6 months at RT is less than 1000 cfu/ml. A liquefied biomass material is deemed to be fermentable if it is at least as effective as corn starch hydrolysate having the same hexose content in the production of ethanol using *S. cerevisiae*.

In another aspect of the invention the minimal 0.2-15% (v/v) concentration of chemical or biological preservatives and industrial storage conditions are sufficient to prevent spoilage of liquefied biomass in excess of 4 months. It was demonstrated that the concentration of the chemical or the biologically derived preservatives used in the described processes has no significant influence on downstream fermentation procedures to produce value adding chemicals, provided pH and organic solvent concentration meet the specification of the desired fermentation procedure. In order to adjust these parameters for the desired fermentation procedure preservatives can alternatively be removed using energy efficient methods such as precipitation of acid and bases or solvent removal using pressure swing rectification.

In a particular aspect of the invention it was demonstrated that the liquefied and preserved sugar beet/sugar cane biomass was an excellent component of industrial fermentation media for bacterial, yeast and fungal organisms producing value adding products such as enzymes, pharmaceuticals or chemical products.

Examples of microorganisms for the fermentation of liquefied sugar beet/sugar cane biomass after pH adjustment comprise but are not limited to bacteria, yeast or filamentous fungi.

In a preferred embodiment of the invention, the microorganisms are selected from the group of *Bacillus* sp., *Lactobacillus* sp., *Bifidobacterium* sp., *Clostridium* sp., *Escherichia* sp. *Propionibacterium* sp., *Acetobacter* sp., *Gluconobacter* sp., *Corynebacterium* (*Brevibacterium*) sp., *Cryptococcus* sp., *Achromobacter* sp., *Streptomyces* sp., *Streptococcus* sp., *Pseudomonas* sp., *Erwinia* sp., *Xanthomonas* sp., *Leuconostoc* sp, or *Ralstonia* sp.

In another preferred embodiment of the invention, the microorganisms are selected from the group of *Saccharomyces* sp., *Schizosaccharomyces* sp., *Candida utilis*, *Mucor* sp., *Torulopsis* sp., *Pichia* sp., *Hansenula* sp, or *Rhodotorula* sp.

Value-added products resulting from bacterial fermentation (Schmid, 2006) of liquefied sugar beet/sugar cane biomass comprise but are not limited to organic acids (e.g. acetic acid, lactic acid, fumaric acid, propionic acid, and glucuronic acid), amino acids (e.g. glutamic acid, leucine, lysine, threonine, aspartic acid, phenylalanine, cysteine), caprolactams (e.g. alpha-amino-caprolactam), antibiotics (e.g. bleomycin, virginiamycin, lincomycin, monensin, blasticidin, tetracycline), vitamins (e.g. vitamin B2, B12 and C), enzymes, nucleotides/nuleosides (e.g. NADH, ATP, cAMP, FAD, coenzyme A), biopolymers (e.g. polyhydroxybutyrate, polyarnides/fibroins), polysaccharides (e.g. xanthan, dextran), amino glucans (e.g. hyaluronic acid) as well as organic solvents and biofuels (e.g. acetone, ethanol, butanol, propanediol).

Value adding products (Schmid, 2006) resulting from yeast fermentation of liquefied sugar beet/sugar cane biomass comprise but are not limited to organic solvents (e.g. ethanol, propanol), nucleotides (e.g. RNA), biosurfactants (e.g. sophorose lipids), enzymes, and biopolymers (e.g. spidroins).

Examples of fungal fermentations using liquefied and preserved sugar beet/sugar cane biomass as a medium after minimal pH adjustment comprise but are not limited to *Aspergillus* sp, *Trichoderma* sp., *Penicillium* sp., *Acremonium* sp., *Rhizopus* sp. and *Talaromyces* sp.

Value adding products resulting from fungal fermentation (Schmid, 2006) with liquefied sugar beet/sugar cane biomass comprise but are not limited to organic acids (citric acid, fumaric acid), antibiotics (e.g. penicillin, cephalosporin), enzymes, and polysaccharides (e.g. chitin).

Preferred fermentation processes include:

A fermentation process, wherein the liquefied biomass is subjected to fermentation using *S. cerevisiae* to produce ethanol.

A fermentation process, wherein the strain belongs to the genus *Clostridium* and wherein the fermentation product is n-butanol, acetone or ethanol.

A fermentation process, wherein the strain belongs to the genus *Escherichia* and wherein the fermentation product is a recombinant enzyme or a biochemical such as an organic acid, an amino acid, or an alcohol.

A fermentation process, wherein the strain belongs to the genus *Propionibacterium* and wherein the fermentation product is propionic acid.

A fermentation process, wherein the strain belongs to the genus *Corynebacterium* and wherein the fermentation product is an amino acid.

A fermentation process, wherein the strain belongs to the genus *Aspergillus* and wherein the fermentation product is an organic acid or an enzyme.

A fermentation process, wherein the strain belongs to the genus *Lactobacillus* and wherein the fermentation product is an organic acid.

In a preferred embodiment, the solid biomass is concurrently liquefied using an enzyme mixture and inoculated with a microorganism, such as yeast (e.g. *S. cerevisiae*) resulting in a one step liquefaction and fermentation process. Preferably the major fermentation product (e.g. ethanol) will be present at a concentration rendering the entire process liquid storage stable.

In another preferred embodiment, the liquefied biomass is subjected to fermentation using a yeast, fungal or bacterial strain capable of producing an alcohol or an organic acid and wherein the alcohol or organic acid is separated from the fermentation broth by (i) stripping the alcohol or organic acid from the fermentation broth. In a particularly preferred embodiment, the liquefied biomass is subjected to fermentation using a yeast, fungal or bacterial strain capable of producing an alcohol and wherein the alcohol is separated from the fermentation broth by (i) stripping the alcohol from the fermentation broth, preferably using carbon dioxide or air or a mixture thereof, (ii) adsorption of the alcohol onto an adsorber material, and (iii) subsequent desorption of the alcohol from the adsorber material.

EXAMPLES

The following examples are for illustrative purposes only and are not to be construed as limiting the invention.

Example 1

Enzymatic Liquefaction of Whole Sugar Beet

Whole sugar beet material was prepared from fresh sugar beet roots sampled in Sulzemoos, Germany. Beet roots were washed to remove remaining soil and cut into 10 mm×10 mm pieces (cossettes) using a Waring blender. The sugar beet material on average had a d.s. content of 24.7%.

The following enzymes were used: arabinase (E-EARAB, Megazymes Inc., Ireland), arabinofucosidase (E-AFASE, Megazymes Inc., Ireland), xylanase (E-XYTR1, Megazymes Inc., Ireland), polygalacturonidase (E-PGALUSP, Megazymes Inc., Ireland), cellulase (Celluclast, Novozymes, Denmark; containing CBH I, CBH II, EG I, EG II, BGL, endo-xylanase activities), Cellulase B (Ecostone Cellulase, AB Enzymes GmbH, Darmstadt, Germany; *T. reesei* enzyme preparation, containing CBH I, CBH II, EG I, EG II, BGL, endo-xylanase activities), beta-glucosidase (Novo 188, Novozymes, Denmark), and pectinase (Pectinex Ultra SP-L, Novozymes, Denmark; containing pectin lyase, arabinofucosidase, endo-arabinase, endo-xylanase, pectate lyase, pectinmethylesterase and polygalacturonidase activities). Where necessary, enzymes were desalted and concentrated with 45 ml sodium acetate buffer (50 mM, pH 5) using 50 ml Amicon ultrafiltration devices (10 kDa cut-off; Millipore, Maidstone, UK).

Furthermore, the following enzymes were used: cellulase enzyme preparation derived from *Trichoderma reesei* (ATCC 56764, 60787); pectinase enzyme preparation derived from *Aspergillus niger* (DSMZ: 737, DSM 7840); pectinase enzyme preparation derived from *Aspergillus aceulatus* (CBS 589.94); beta-glucosidase enzyme preparation derived from *Aspergillus niger* (DSMZ 737).

Protein concentrations were determined by the Bradford method (Bradford, 1976), Endo- and exo-cellulase activities were measured using p-nitrophenyl-beta-D-cellobioside (Wood and Bhat, K., 1988). Arabinofuranosidase activity was determined using 4-nitrophenyl-alpha-L-arabinofuranoside (pNP-Araf) (Taylor et al., 2006). Xylosidase activity was determined using o-nitrophenol substituted-beta-D-xylopyranoside (Chen et al., 1986; Taguchi et al., 1996).

Example 1.1

Liquefaction of Sugar Beet Biomass Under Technical Conditions

The following enzyme mixture was prepared:
0.8 ml Celluclast (0.5% w/w d.s.), 0.13 ml Novo 188 (0.1% w/w d.s.), 3.7 ml Pectinex Ultra SP-L (0.5% w/w d.s.), 30.4 ml 50 mM NaAc buffer (pH 5).

This enzyme mixture was mixed with fresh sugar beet material (cossettes) in various mass ratios (0-0.1% (w/w) Enzyme/Substrate, E/S). The final reaction mixture contained 15% d.s. of sugar beet material. The mixture was incubated without any further mechanical treatment at 45° C. for 6 hours. After the incubation the sugar beet biomass was almost completely liquefied. Only 0.35% (w/w) of the initial sugar beet biomass remained as insoluble solids as determined by IR balance measurements. The resulting slurry was filtered through a 0.2 µm nylon filter and 100 µl were subsequently applied to HPLC analysis. The resulting hydrolysis mixture was analyzed by HPLC (Agilent, Germany) with an. Aminex HPX 87 (BioRad Labs, Hercules, USA) ion exchange column (Eluent: 100% water, T: 85° C., Flow: 0.6 ml/min, RI detection). The resulting saccharide composition in the supernatant over various enzyme dosing ratios is shown in FIG. 1. The data show that the liquefaction process was completed in 6 hours which distinguishes the process from prior art where a minimum of 20 hours was required for liquefaction (de Baynast et al., 1989).

The results also indicate further mechanical energy input is not required before or during the sugar beet liquefaction step. The process does not require grinding of the biomass for efficient biomass liquefaction. Under the experimental complete liquefaction and a quantitative release of all sugar components from sugar beet biomass is achieved. A dosing of 0.1% E/S results in efficient liquefaction.

Example 2

Biomass Liquefaction and Preservation

Example 2.1

Biomass Liquefaction and Chemical Preservation

Mineral acid ($H_2SO_4$) was used to chemically preserve liquefied sugar beet and to prevent microbial growth without affecting enzymatic biomass liquefaction and hydrolysis.

Figure 2:
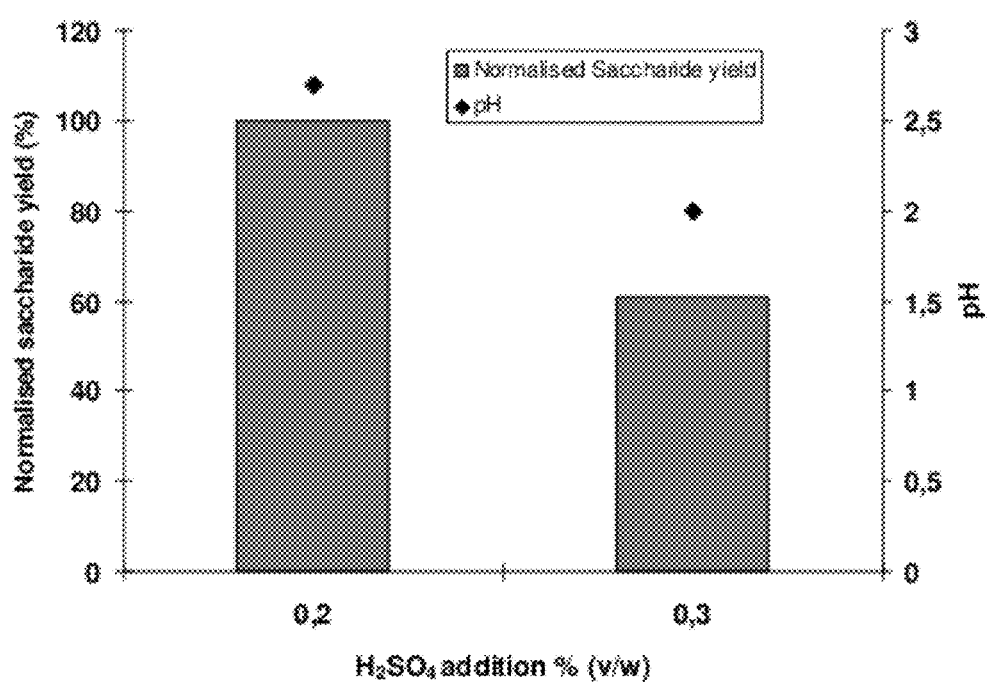
FIG. 2 shows the effect of $H_2SO_4$ addition on saccharide yield and reaction pH.

Effect of $H_2SO_4$ concentration and addition time on enzymatic liquefaction performance: Fresh sugar beet biomass was prepared as described above. To initiate sugar beet biomass (20 g; final 20% (w/w d.s.)) liquefaction an enzyme preparation (0.1% E/S) was added containing the following activities: 50% (w/w) pectinase, 50% (w/w) cellulase, 4 CBU/ml beta-glucosidase. In addition the feedstock was dosed with different concentrations of $H_2SO_4$ (0.2%, 0.3% (v/w)). The liquefaction was then carried out in a closed Erlenmeyer flask over 7 days at 45° C. without mixing. After the 7 day incubation period, the process of enzymatic liquefaction in the presence of $H_2SO_4$ was determined using standard HPLC procedures (see above). Data are shown in FIG. 2. The acid was added at the start of the enzymatic reaction. The addition of 0.2% (v/w) $H_2SO_4$ (pH 2.5) lead to complete liquefaction of the beet biomass. Surprisingly the enzymatic liquefaction could be carried out at a pH of 2.5.

Example 2.2

Biomass Liquefaction and Biological Preservation with *Lactobacilli* (Lactic Acid Induced Ensiling)

Figure 3:
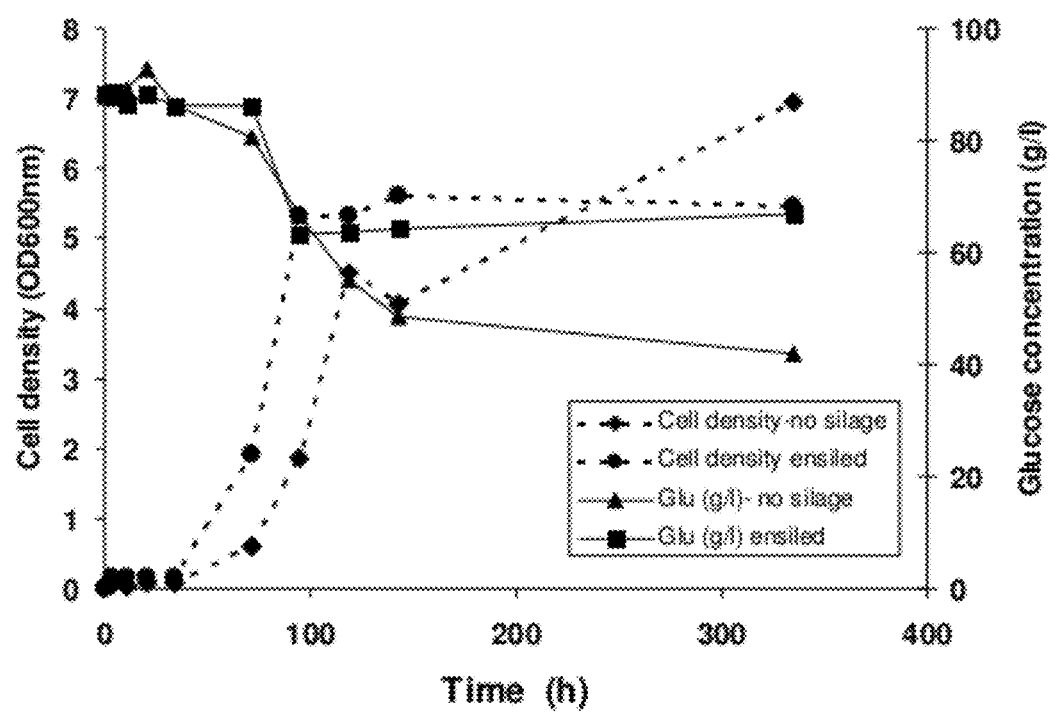
FIG. 3 shows the microbial growth and glucose profiles of unsterilized sugar beet hydrolysate (SBH) with (ensiled) and without (no silage) addition of *Lactobacillus amylovorus*.

Stable fermentation feedstock was generated from sugar beet biomass by concurrent liquefaction and lactic acid induced preservation (ensiling). *Lactobacillus* cultures (*Lactobacillus amylovorus*, DSMZ 16698) were activated on MRS medium containing additional 5% (w/w) glucose. Fresh sugar beet biomass was prepared as described above. To induce biomass (20% (w/w)) liquefaction, an enzyme preparation was added containing the following activities: 0.25% pectinase, 0.25% cellulase, 4 CBU/ml beta-glucosidase (dosing: 0.1% E/S). Sugar beet biomass was concurrently inoculated with *Lactobacillus* cultures ($OD_{600nm}$=0.1) (ensiled biomass hydrolysate) or, alternatively, not inoculated (control, non-ensiled). Concurrent biomass liquefaction/microbial cultivation was carried out under anaerobic conditions in Erlenmayer flasks at 40° C. for 350 hours. Surprisingly, the addition of the microbial culture had no effect on the enzymatic liquefaction process which was completed under the experimental conditions within 72 hours. During the entire incubation time microbial cell growth was followed spectrometrically at $OD_{600nm}$ while glucose concentration was monitored by HPLC. The pH of both ensiled and non-ensiled biomass hydrolysates slightly decreased from pH 4 to 3.5 which is related to the release of acidic metabolites like lactic and acetic acid. Data in FIG. 3 show that in the ensiled sample (*Lactobacillus* treated) cell growth is faster than in the non-ensiled control but stopped after 95 hours incubation period. By contrast in the non-ensiled control cell growth continues until the end of the sampling period. Most importantly in the non-ensiled control continued cell growth results in 50% (w/v) loss of glucose at the end of the sampling time. The data show that concurrent enzymatic liquefaction and biological ensiling with *Lactobacilli* is a feasible method to preserve ~90% (w/v) of sugars in the sugar beet hydrolysate (fermentation medium).

Figure 4:
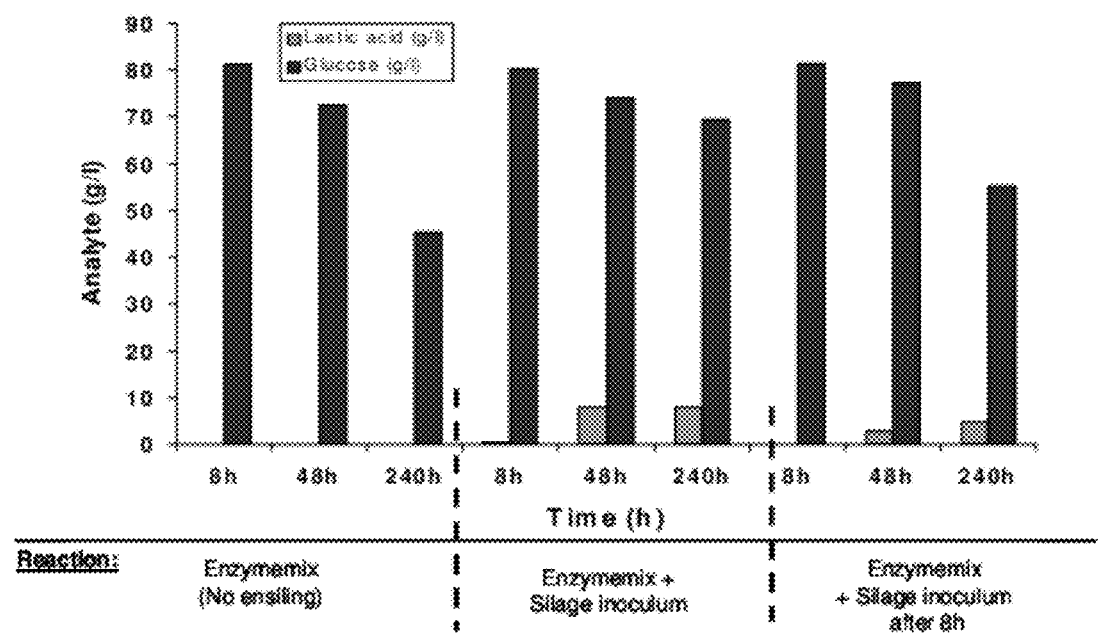
FIG. 4 shows a comparison of concurrent/sequential enzymatic liquefaction and ensiling procedures.

Microbial preservation has been examined in another experimental series with *Lactobacilli* inoculation. The amount of treated biomass and the applied enzyme cocktail for liquefaction are equivalent to experiments described above. Experimental conditions:
1. Enzyme mixture (Enzymatic liquefaction only, no ensiling; control);
2. Enzyme mixture+ensiling *Lactobacillus* addition ($OD_{600nm}$=0.1) after 0 hours liquefaction
3. Enzyme mixture+ensiling *Lactobacillus* addition ($OD_{600nm}$=0.1) after 8 hours liquefaction The process of biomass liquefaction and preservation procedures was monitored for glucose, and lactic acid by HPLC after 8, 48 and 240 hours. Cumulative results are shown in FIG. 4. The data show that in the absence of ensiling *lactobacillus* cultures, the glucose content rapidly declines. Direct addition of ensiling *Lactobacillus* cultures lead to rapid lactic acid formation and limited glucose losses (~10% (w/v)) confirming lactic acid induced preservation. By contrast addition of ensiling *lactobacillus* cultures 8 hours after initiation of enzymatic liquefaction resulted in less lactic acid production and higher glucose losses.

Example 2.3

Separate Biomass Liquefaction and Chemical Preservation

Mineral acid ($H_2SO_4$) was used to chemically preserve liquefied sugar beet and to prevent microbial growth after enzymatic biomass liquefaction and hydrolysis.

Sugar beet was liquefied as described in example 1.1. H2SO4 was added to the liquefied biomass after 4 h and was incubated at RT in an Erlenmeyer flask, which was fitted with a fermentation tube to release any gaseous substances formed. The sugar content of the liquefied biomass was monitored over 190 days. Samples were taken aseptically at 15, 46, 99 and 190 days and sugar concentrations were measured using HPLC procedures described above. Data in FIG. 8 shows that no loss of sugars could be detected over the sampling period, which indicates that long term preservation of liquefied sugar beet biomass is achievable by addition of sulphuric acid to a final concentration of 0.5 or 1% v/v. The pH of the preserved biomass was determined to be 1.33 and 1 for the samples containing 0.5 or 1% H2SO4% v/v respectively.

Example 3

Liquefied Sugar Beet Biomass as a Fermentation Medium

Example 3.1

Production of Acetone, Butanol and Ethanol

Sugar beet hydrolysate was prepared as described in Example 1.1. *Clostridium saccharobutylicum* (DSMZ 13864, Inoculum $OD_{600nm}$=1) was added to a fermentation medium containing 15% (w/v) sugar beet hydrolysate as the sole carbon source.

Figure 5:
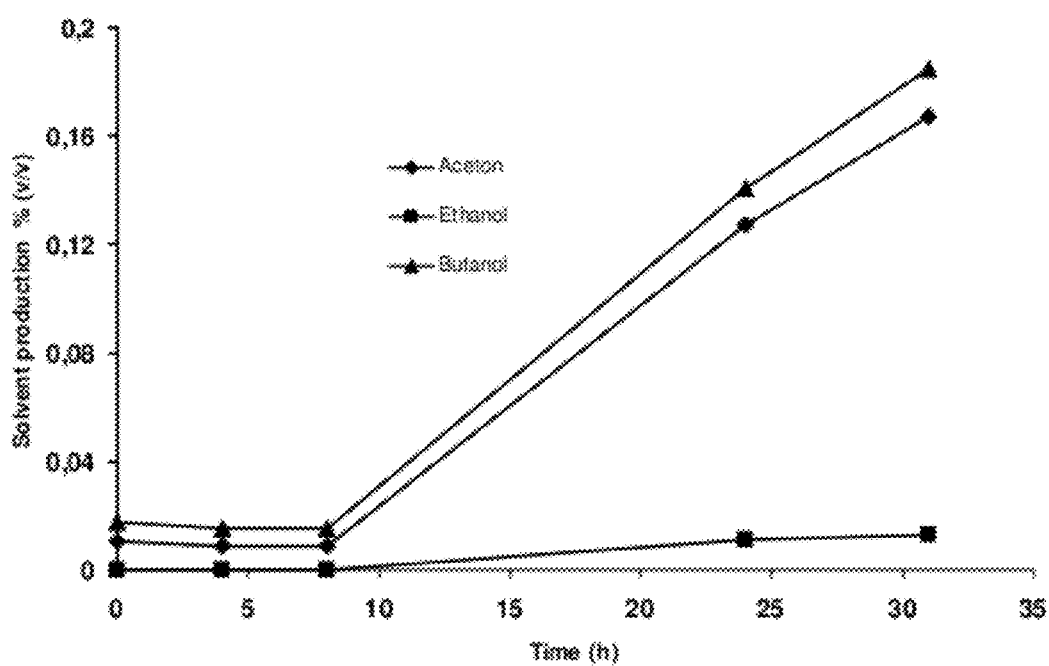
FIG. 5 shows the pH profile and cell growth of *Clostridium saccharobutylicum* (DSMZ 13864) on liquefied sugar beet medium.
Figure 6:
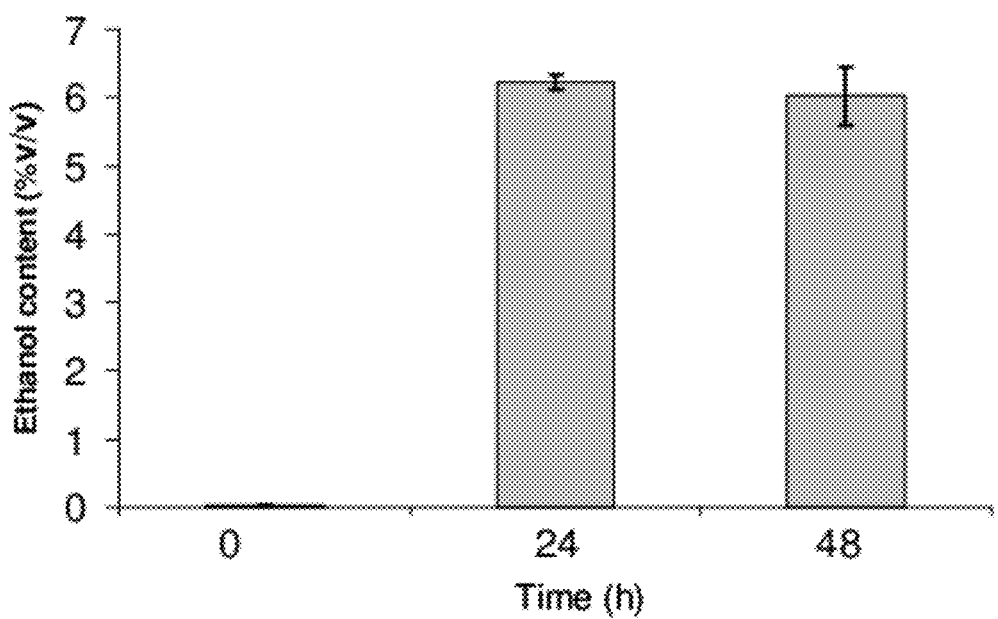
FIG. 6 shows ABE production by *Clostridium saccharobutylicum* (DSMZ 13864) on liquefied sugar beet medium.

Medium composition: 15% (w/v) sugar beet hydrolysate, 6 g/l tryptone peptone (BD), 2 g/l yeast extract, 3 g/l $NH_4CH_3COO^-$, 0.3 g/l $MgSO_4$, 0.5 g/l $KH_2PO_4$, 0.01 g/l $FeSO_4 \times 7\,H_2O$, 0.2 g/l biotin, 1 g/l p-aminobenzoic acid, 1 g/l thiaminechloridhydrochloride, 1 mg/l Resazurin. The fermentation was carried out over 40 h at 35° C. and pH 6.5. Biomass was determined via $OD_{600nm}$ measurements and pH was measured. Samples were subsequently centrifuged at 12,000 rpm for 5 min. The resulting supernatants were analyzed using GC analysis to determine acetone, butanol and ethanol concentrations in the reaction mixture. FIG. 5 shows the pH profile and cell density development during the fermentation procedure. FIG. 6 shows the formation of solvents. The data demonstrate that solvent production is feasible when appropriate *Clostridia* strains are grown on sugar beet hydrolysate based media.

The butanol was furthermore purified by in-situ adsorption of butanol out of the vapour phase onto an adsorber. The adsorption is conducted at ambient temperatures, which reduces the energy demand for recovery significantly compared to conventional methods. Butanol is removed from the adsorber by heating the adsorbent and collected by cooling the containing butanol vapour coming off the adsorber in a condenser. Compared to a gas stripping process the concentration of the organic molecule with this method is significantly higher due to the selectivity of the adsorber for the organic molecule. Butanol recovery from the fermentation medium was achieved using a butanol adsorption/desorption process mediated by a zeolite material. For this process a MFI zeolite was prepared according to U.S. Pat. No. 7,244,409. Butanol was adsorbed from the overhead vapour phase of ABE fermentation (in a closed system) broth. Butanol adsorbed to the zeolite was desorbed (recovered) by heating the adsorbent. The vapour coming off the flask was condensed in a condenser and collected. The overall butanol content in the condensate was 67%.

Example 3.2

Ethanol Production with S. Cerevisiae Using Crude Beet Hydrolysate as a Carbon Source Sugar beet hydrolysate was prepared as described above and used as the sole fermentation medium component for ethanol production with S. cerevisiae (DSMZ 1333).

Figure 7:
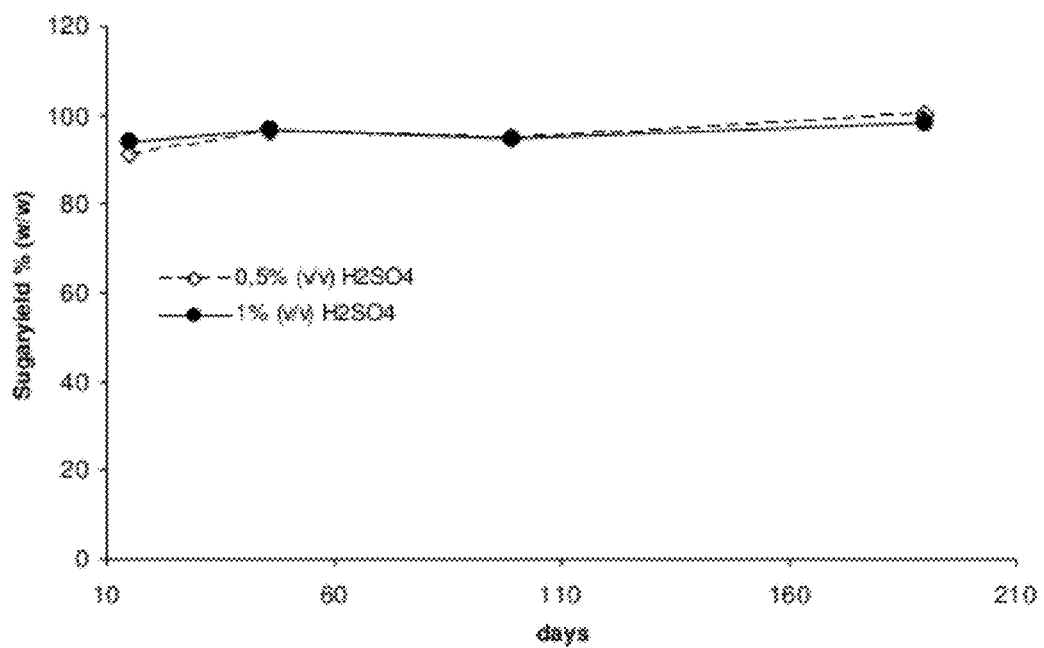
FIG. 7 shows ethanolic fermentation of sugar beet hydrolysate using *S. cerevisiae*.

Undiluted and unsterilized sugar beet hydrolysate (30 ml) was inoculated with 1 g/l S. cerevisiae cells. Fermentations were carried out in 100 ml shake flasks, which were incubated at 28° C. (200 rpm) for 48 hours. A negative control was included with uninoculated beet hydrolysate medium. Ethanol concentrations were determined at 24 and 48 hours using GC-analysis (Sillers et al., 2008). No ethanol formation could be detected after the 48 hours incubation time in the negative control sample. FIG. 7 shows the results of the ethanolic fermentation. The fermentation resulted in an ethanol yield of 64% (w/v) based on glucose contained in raw beet hydrolysate (13-15% (w/v)). This result indicated that enzymatic sugar beet hydrolysate can be used directly in ethanolic fermentations without the need of further treatment of the hydrolysate.

REFERENCES

Bradford M. M. (1976) A rapid and Sensitive Method for the Quantitation of Microgram Quantities of Protein Utilizing the Principle of Protein-Dye Binding. Anal. Biochem. 72, 248-254

Chen W. P., Matsuo M., Yasui T. (1986) Agric. Biol. Che, 50, pp. 1183-1194

De Baynast, De Septfantaines R., Brouard F., Baret J.-L., Gicquiaux Y., Olsen H. (1988) Process for the liquefaction of beets and chicory roots by enzymatic hydrolysis and liquid hydrolysate. U.S. Pat. No. 4,886,672

Ezeji T. C. Qureshi N., Blaschek H. P. (2004) Butanol fermentation research: upstream and downstream manipulations. Chem Rec, Vol. 4, No. 5, pp. 305-314

Ting X., Zhang X., Bao T. (2009) Inhibitor performance of lignocellulose degradation products on industrial cellulose enzymes during cellulose hydrolysis. Appl. Biochem. Biotechnol., DOI 10.1007/s12010-009-8525-z (ahead of print)

Oosterveld A., Beldmann G., Voragen A. G. J., (2002) Enzymatic modification of pectic polysaccharides obtained from sugar beet pulp. Carbohydrate Polymers 48, pp. 73-81

Sakamoto T., Sakai T. (1995) Analysis and structure of sugar-beet pectins by enzymatic methods. Phytochemistry 39, pp. 821-823

Schmid R. D. (2006) Pocket Guide to Biotechnology and Genetic Engin. Wiley-VCH edts.

Sillers R., Chow A., Tracy B., Papoutskis E. T. (2008) Metabolic engineering of the non-solvatogenic Clostridium acetobutyricum strain M5 to produce butanol without acetone demonstrate the robustness of the acid-formation pathways and the importance of electron balance. Metabol Engineer. 10, pp. 321-332

Spagnuolo M., Crecchio C., Pizigallo M. D. R., Ruggiero. (1997) Synergistic effects of cellolytic and pectolytic enzymes in degrading sugar beet pulp. Bioresour. Technol. 60, pp. 215-222

Taguchi H.; Hamasaki T., Akamatsu T, Okada H. (1996) A simple assay for xylanase using o-nitrophenyl-β-D-xylobioside. Bioscience, Biotechnology, and Biochemistry, 60, pp. 983-985

Woskow and Glatz (1991) Propionic acid production by a propionic acid-tolerant strain of Propionibacterium acidipropionici in Batch and semicontinous fermentation. Appl. Envir. Microbiol. 57, pp. 2821-2828

Wood T. M., Baht K. M., (1989) Methods for measuring cellulose activities. Methods in Enzymology. 160, pp. 87-112

The invention claimed is:

1. Process for the production of a liquefied product, comprising the following steps:
   (a) providing sugar beet and/or sugar cane biomass material;
   (b) liquefying said biomass by subjecting it to the enzymatic action of an enzyme mixture comprising cellobiohydrolase, beta-glucosidase, and polygalacturonase to a liquefied product;
   wherein the enzyme mixture additionally contains arabinose,
   wherein step (b) is carried out for less than 10 hours and
   wherein the liquefied product in step (b) has a content of remaining insoluble solids of less than 2% (w/w).

2. The process according to claim 1, wherein a chemical or microorganism is added before or during step (b) to render the liquefied product storage stable.

3. The process according to claim 2, wherein the chemical is selected from the group consisting of inorganic acid, inorganic anhydrides or wherein the microorganism is one or more selected from Lactobacillus, Lactococcus, Bacillus, Saccharomyces, and Clostridium.

4. The process according to claim 1, wherein enzyme mixture is used in an amount of 0.025 to 0.1% (w/w) of the biomass.

5. The process according to claim 1, wherein enzyme mixture contains 1 to 4% (w/w) cellobiohydrolase, 1 to 4% (w/w) beta-glucosidase, and 35 to 45% (w/w) polygalacturonase, with respect to the total weight of the enzyme mixture.

6. The process according to claim 1, wherein no mechanical size reduction is carried out during process step (b).

7. The process according to claim 1, wherein the enzyme mixture additionally contains pectinmethylesterase activity.

8. The process according to claim 1, which is carried out in a single tank.

9. The process according to claim 2, wherein the chemical or microorganisms are added to the solid biomass before or together with the enzyme mixture.

10. Liquefied biomass derived from sugar beet and/or sugar cane, which is storage stable and fermentable and obtainable by a process as defined in claim 1.

11. The liquefied biomass according to claim 10, having a saccharose content of 0 to 50% (w/w), a fructose content of 20 to 45% (w/w), and a glucose content of 50 to 70% (w/w).

12. The process according to claim 2, wherein the chemical or microorganism is added in an amount to adjust the pH of the liquefied biomass to a pH below 3.

13. The process according to claim 1, wherein step (b) is carried out for 6 hours or less.

14. Process for the production of a liquefied product, comprising the following steps:

(a) providing sugar beet and/or sugar cane biomass material;
(b) liquefying said biomass by subjecting it to the enzymatic action of an enzyme mixture comprising cellobiohydrolase, beta-glucosidase, and polygalacturonase to a liquefied product;

wherein the enzyme mixture additionally contains one or more hemicellulase activities selected among arabinase, xylanase, rhamnogalacturonase and 1,3-/1,6-beta-D-glucanase;

wherein step (b) is carried out for less than 10 hours; and wherein the liquefied product in step (b) has a content of remaining insoluble solids of less than 2% (w/w).

* * * * *